April 28, 1936.
L. B. LE DUKE
Plant Pat. 175
PEACH TREE
Filed Feb. 4, 1935
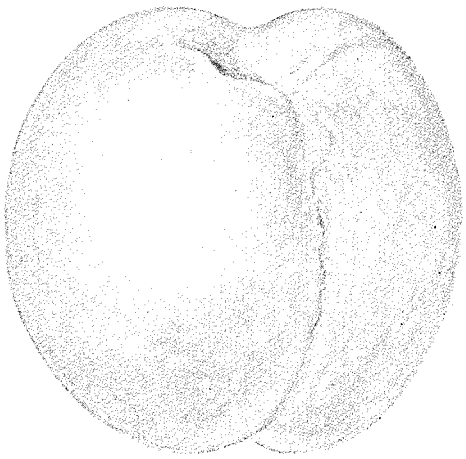
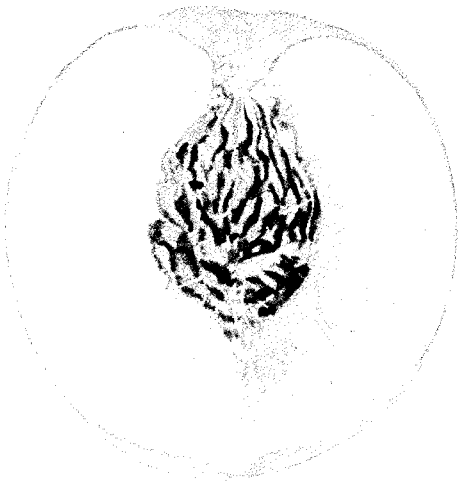
INVENTOR
Lawrence Bellmie Le Duke
By Orville M. Kile
PLANT PATENT AGENT Patented Apr. 28, 1936 Plant Pat. 175

UNITED STATES PATENT OFFICE

175

PEACH TREE

Lawrence Bellinie Le Duke, Lawrence, Mich., assignor to Greening Nursery Company, Monroe, Mich., a corporation Application February 4, 1935, Serial No. 4,924

1 Claim. (Cl. 47—62)

My present invention relates to improvements in freestone peaches of the J. H. Hale type. The tree is somewhat larger than the typical J. H. Hale tree grown under similar conditions, but not quite as large as the typical Elberta tree. The fruit is about the same size and of a quality and coloring somewhat similar to that J. H. Hale, but differing in many particulars as hereinafter detailed. The most notable distinction from the J. H. Hale peach is the self-fertile character of this new variety.

My new variety was first discovered as a sport limb on a J. H. Hale tree. It has been asexually reproduced by grafting and these grafted trees have recently come into bearing, thereby proving the reproductive qualities of this variety. The reproduced fruit is identical in general characteristics with the fruit produced by the original sport limb.

The accompanying illustration shows in full color an average specimen of the fruit of this new variety both in whole and when split in half. The following is a detailed description:

*Tree*

*Size.*—Medium-large, larger than J. H. Hale but not quite as large as Elberta. Much larger than Halberta. Both the J. H. Hale and the Halberta are of semi-dwarf type.

*Vigor.*—Moderately vigorous, stronger grower than J. H. Hale.

*Form.*—Upright, spreading.

*Hardiness.*—Hardier than Elberta and J. H. Hale. Also much more hardy than Halberta.

*Productiveness.*—Productive.

*Trunk.*—Stocky.

*Branchlets.*—Medium thickness and length, internodes medium.

*Bark (on branchlets).*—Dark red over olive green, smooth, glabrous, lenticels conspicuous, numerous, large, raised.

*Leaves.*—5½ to 6 inches long by 1½ to 2 inches wide at widest point, having long, tapering points, rather thick and somewhat leathery, heavy midribs, considerably crinkled, edges scalloped rather than serrated but having a short spine on the anterior edge of each scallop, petioles ⅜ inch long.

Upper surface dark green, lower surface moderately dark grayish green, glands variable in number, position and size; reniform, dark-greenish-yellow.

*Bearing habits.*—This variety bears regularly and produces no small so-called "buttons".

*Flowers*

*Buds.*—Moderately large and plump. Hardier than Elberta or J. H. Hale, but not as hardy as South Haven variety.

*Blossoms.*—Resemble J. H. Hale blossoms in general appearance but are slightly larger and open a little earlier. Free pollen grains are present in the opened blossom in sufficient quantities to make this variety self-fertile. Investigations extending over several years show this variety not only self fertile but producing free pollen capable of setting fruit on other varieties. This variety has never produced small, misformed peaches known as "buttons", a characteristic of self-sterile varieties.

*Fruit*

*Size.*—Very large, about like J. H. Hale, 3½ to 3⅜ inches axial diameter, 3 inches radial diameter.

*Shape.*—Globular but slightly elongated as indicated by dimensions, only slightly bulging on one side (much less than in Elberta), slight apex but latter being located in the suture it does not ordinarily extend beyond the plane of the globular surface.

*Cavity.*—Deep, wide, regular.

*Skin.*—Moderately thick, only slightly pubescent.

*Color.*—Ground is various shades of yellow and showing some green until quite mature. When mature the ground is Apricot yellow (Plate IV, Ridgway's Color Standards and Nomenclature). Usually about one-half the surface is overspread with touches and at points blotches of red. The red is dull in tone and varies from Pompeian red (Plate XIII) to the lighter shades such as Jasper red (Plate XIII). Some of the latter occurs in flecks and spots and even as faint stripes at points. This is not a highly colored variety. A gray bloom further obscures the coloring.

*Flesh.*—Yellow, shading from Apricot yellow to Lemon chrome (Plate IV), and moderately red at the pit; juicy, fine grained, tender, moderately firm, slightly stringy. Flavor is sweet to subacid and of pleasing quality.

*Stone.*—Free 1¾ inches long, 1¼ inches wide, usually slightly larger than the stone of J. H. Hale and slightly smaller than that of Elberta; oval, pointed at apex, the two portions being unequal in size. The surfaces are deeply grooved and pitted, the dorsal suture deeply grooved and somewhat winged.

*Maturity.*—This new variety matures three to five days later than the J. H. Hale grown under comparable conditions. It apparently matures about three days earlier than Halberta.

Having thus disclosed my invention, I claim:

The variety of peach tree described herewith, characterized particularly by being self-fertile, and bearing fruit of the J. H. Hale type but differing from that variety in numerous particulars as described and illustrated.

LAWRENCE BELLINIE LE DUKE.